United States Patent [19]
Gupta

[11] Patent Number: 5,718,684
[45] Date of Patent: Feb. 17, 1998

[54] MULTI-LOBED BALLOON CATHETER

[76] Inventor: Mukesh Gupta, 6958 Highland Park Dr., Nashville, Tenn. 37205

[21] Appl. No.: 653,331

[22] Filed: May 24, 1996

[51] Int. Cl.$^6$ .................................. A61M 29/00
[52] U.S. Cl. .................................. 604/96; 606/194
[58] Field of Search ................ 604/96, 97, 100, 604/101, 280, 282; 606/191–194

[56] References Cited

U.S. PATENT DOCUMENTS

| | | |
|---|---|---|
| 4,581,017 | 4/1986 | Sahota . |
| 4,796,629 | 1/1989 | Grayzel ........................ 604/96 X |
| 4,983,167 | 1/1991 | Sahota . |
| 5,019,042 | 5/1991 | Sahota . |
| 5,071,406 | 12/1991 | Jang . |
| 5,147,302 | 9/1992 | Euteneuer et al. . |
| 5,318,587 | 6/1994 | Davey . |
| 5,348,538 | 9/1994 | Wang et al. . |
| 5,458,572 | 10/1995 | Campbell et al. ................ 604/96 |
| 5,458,575 | 10/1995 | Wang .......................... 606/194 X |

OTHER PUBLICATIONS

Balloon mitral valvotomy with a single catheter: a comparison between bifoil/trefoil and the Inoue balloon; European Heart Journal (1993) 14, 1065–1071; J.J. Patel, A.S. Mitha, S. Chetty and J.S. Hung.

*Primary Examiner*—John D. Yasko
*Attorney, Agent, or Firm*—Polster, Lieder, Woodruff & Lucchesi, L.C.

[57] ABSTRACT

A dilation catheter for treating stenotic regions within a body lumen includes a multi-lobed balloon, the lobes of which extend longitudinally of a catheter robe. The lobes of the balloon of this catheter, when inflated inside the coronary artery stenosis prevent slippage of the balloon into the soft region of the stenosis and cause cracks in the hard region of the stenosis as well. The lobes of the balloon exert interrupted radial compression inside the stenosis. The interrupted radial compression increases the number of cracks in the stenosis.

4 Claims, 1 Drawing Sheet

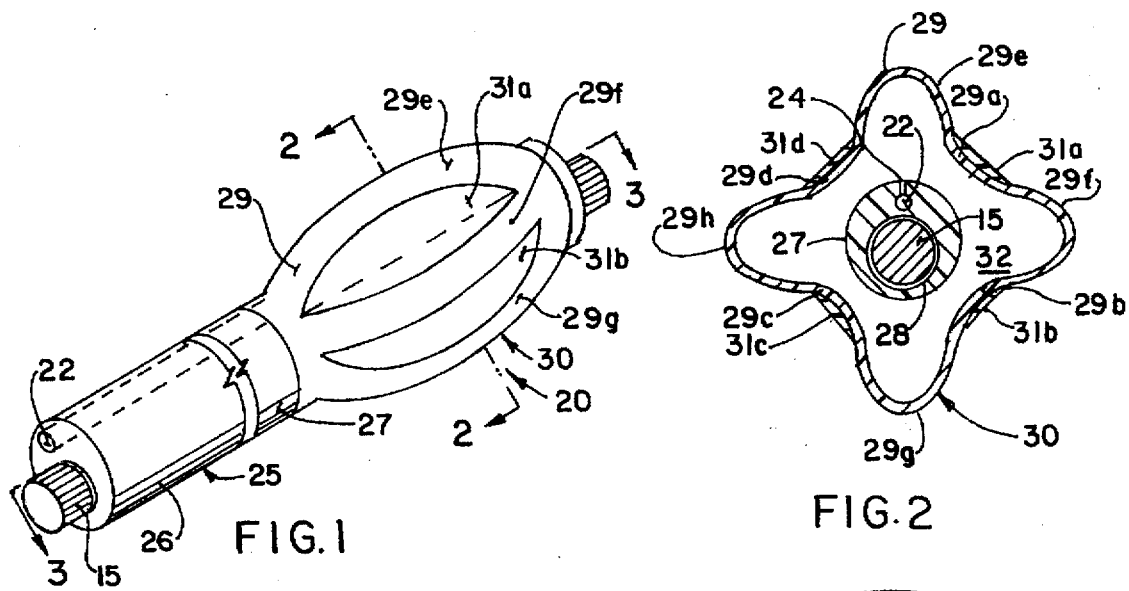
FIG. 1
FIG. 2
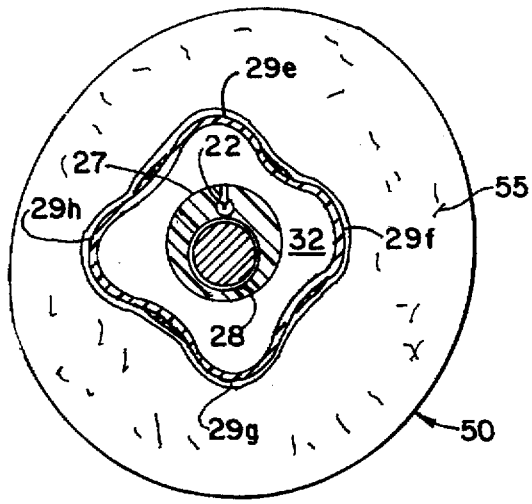
FIG. 2A
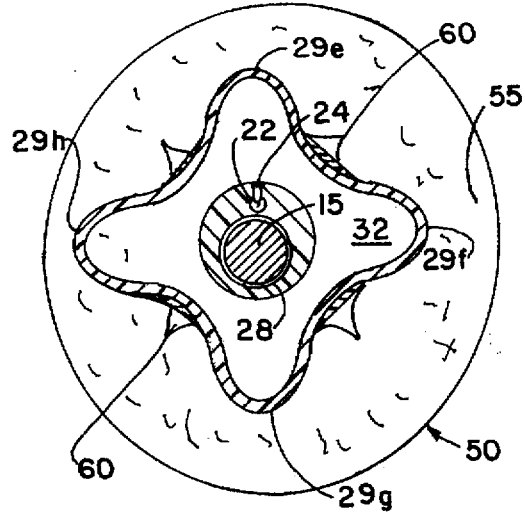
FIG. 2B
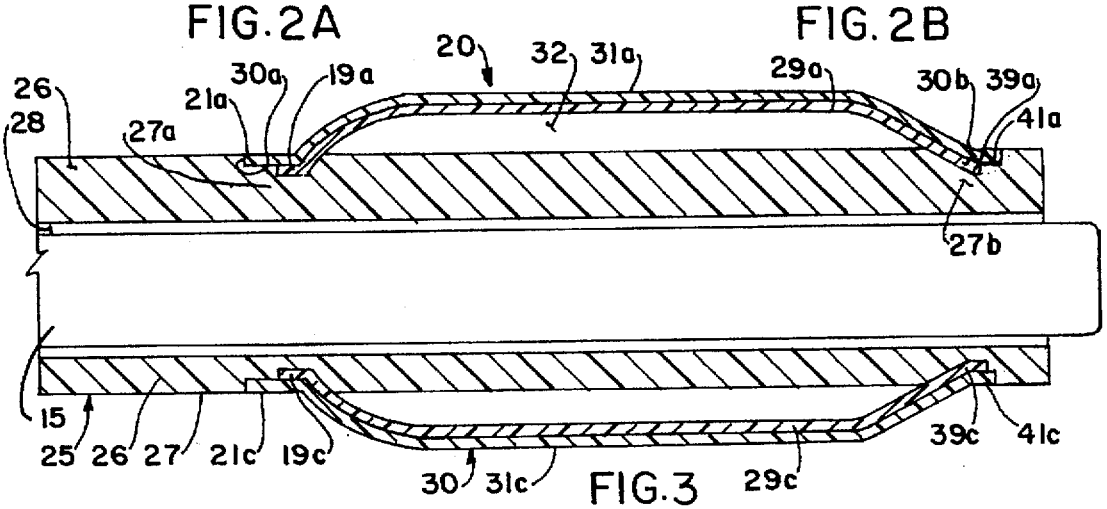
FIG. 3

MULTI-LOBED BALLOON CATHETER

BACKGROUND OF THE INVENTION

This invention relates to balloon catheters and specifically to the field of dilation catheters for use in treatment of stenotic regions or to widen a constricted blood flow through a tubular passage, such as the coronary artery, aorta, as well as other blood vessels and heart valves or other constrictions, for example urethral stricture, in the human body.

Coronary angioplasty, a procedure for treating a patient having a stenosis or constricted blood region in a coronary artery, has become a widely accepted therapeutic alternative to coronary bypass surgery. It has certainly resulted in reduction of morbidity. Coronary angioplasty involves insertion of a balloon inside a stenosis and inflating the balloon. The inflated balloon dilates the flow passage or the lumen which had been constricted by the stenosis hence restoring the blood flow through the coronary artery.

Coronary angioplasty begins with the insertion of a guiding catheter, or a sleeve into a distant artery, for example a femoral artery. The guiding catheter is advanced into the obstructed artery under direct X-ray visualization and its distal tip positioned proximal to the stenosis. Often a guide wire is inserted through the guiding catheter and its distal tip advanced through the stenosis. A balloon angioplasty or a balloon dilation catheter, which has a balloon attached to its shaft or robe, is advanced over the guide wire. The balloon of the balloon dilation catheter is positioned inside the stenosis and inflated by forcing fluid into the balloon. The inflated balloon compresses the tissue, creating the stenosis, radially outwardly between the balloon and the wall of the lumen. The radial outward compression expands the lumen by at left three following mechanisms:

1. Squeezing the stenosis,
2. Creating cracks in the stenosis, and
3. Stretching the stenosis.

Stenosis is usually composed of soft and hard regions. The soft regions are largely composed of fatty and elastic tissue. The hard regions are largely composed of fibrous tissue and calcium. The hard regions are relatively less elastic as compared to the soft regions. When a conventional balloon is inflated inside a stenosis, the balloon expands more readily inside the soft regions of the plaque. The soft regions of the stenosis, being rich in elastic tissue, also recoil easily alter the inflated balloon is deflated. Hence, there is a loss of lumen at the stenosis site after its dilation by a conventional balloon. After balloon dilation of a stenosis, a cardiologist performing angioplasty checks the blood flow rate through the stenosis. If the blood flow is not adequate, the cardiologist either inflates the balloon catheter to a larger diameter by forcing more fluid in it (if the balloon is compliant) or inserts a balloon catheter having a balloon of larger diameter and inflates it. The larger balloon makes the cracks deeper. Larger cracks may progress to dissection or rupture the artery. Dissection refers to extension of crack into or beyond the middle layer of an artery called the 'media'. Blood clots in the dissection may obliterate the lumen of the artery. Both dissection and rupture of a coronary artery can lead to heart attack and even death.

Some of these problems have been recognized and addressed in a number of U.S. patents, among them Sahota U.S. Pat. No. 4,983,167, addressing the problem of continuing the flow of blood during inflation of the balloon, and Sahota U.S. Pat. No. 5,019,042, addressing the problem of treating hardened or calcified stenotic portions within a body lumen.

SUMMARY OF THE INVENTION

The multi-lobed balloon dilation catheters of the present invention overcome many of the difficulties associated with ordinary prior art balloon dilation catheters, specifically during their use in coronary artery dilation. The balloon of the multi-lobed balloon catheter of the present invention has a multiplicity of lobes arranged parallel to the long axis of the catheter shaft and appear like a flower in cross section. The lobes of the multi-lobed balloon catheter exert interrupted radial compression pressure on stenosis, higher in areas in contact with the lobes and lower in areas in between the lobes. These interrupted zones of high and low radial compression pressure increase the number of cracks in the stenosis compared to prior art balloon dilation catheters. To obtain a desired post dilation lumen, the multi-lobed balloon dilation catheters of present invention create more superficial cracks and fewer deeper cracks than are created by prior art balloon dilation catheters. Superficial cracks are less likely to progress into dissections or rupture the artery, hence reducing the danger of heart attack and even death. Besides, superficial cracks cause less injury to the deeper layer, media, of the blood vessel. Less injury to media leads to lesser proliferation of vascular smooth muscle cells. Lesser proliferation of vascular smooth muscle cells reduces the risk of restenosis. Furthermore, the multi-lobed balloon dilation catheters of the present invention create more linear (parallel to the long axis of the artery) cracks than spiral or transverse or zig zag cracks created by prior art balloon dilation catheters. Linear cracks reduce the risk of obliteration of the blood flow.

The multi-lobed balloon catheter of the present invention also create cracks in the hard regions of the stenosis. The various lobes of the multi-lobed balloon act as anchors inside the stenosis and prevent slippage of balloon into the soft regions of the stenosis. By dilating the hard regions of the stenosis, which are less likely to recoil, the multi-lobed balloon dilation catheters of the present invention obviate the need for larger dilation catheters, which might be necessary with the use of prior art balloon dilation catheters.

BRIEF DESCRIPTION OF THE DRAWINGS

FIG. 1 is a perspective view of one embodiment of multi-lobed balloon dilation catheter of this invention;

FIG. 2 is an enlarged cross sectional view taken along the line 2—2 of FIG. 1;

FIG. 2a is a schematic operational view in a cross section illustrating the multi-lobed balloon of FIG. 2, partially inflated, inside a hypothetical but not unrealistic coronary artery;

FIG. 2b is a view similar to that of FIG. 2a, illustrating the multi-lobed balloon further inflated; and FIG. 3 is an enlarged longitudinal sectional view taken along the line 3—3 of FIG. 1, also corresponding to the section along the line 3—3 of FIG. 2.

DETAILED DESCRIPTION OF THE EMBODIMENT

The present invention will be illustrated and described as an over-the-wire balloon catheter for use in angioplasty, of the type illustrated in FIGS. 1 through 3. However, it should be understood that the present invention can be applied to fixed-wire catheters including shortened guide wire lumens or to non-over-the-wire balloon catheters. Furthermore, this invention can be applied to dilation catheters intended for use in any and all vascular systems or cavities or in non-vascular cavities of the body. This invention will be described as a catheter having an inflation channel in the wall of the catheter. However, it should be understood that the present invention can be applied to coaxial catheters, wherein the inflation channel is provided by the space between the tubes of the catheter.

Referring now to the drawings in detail, wherein like reference numerals designate like elements, throughout the several views thereof, there is shown generally at 20 in FIG. 1, a multi-lobed balloon dilation catheter embodying the present invention in a preferred form. In general, the multi-lobed balloon dilation catheter assembly 20 of the present invention is comprised of an elongate tubular member (catheter) 25 with an annular wall 26 of sufficient (radial) thickness to permit its being inserted into and pushed through an artery and to accommodate a flow passage 22 extending lengthwise of the catheter between an inside and an outside surface thereof. The catheter 25 is preferably made of a flexible material such as high density polyethylene. The catheter 25 has a distal end portion 27 and a proximal end portion. The inside surface of the annular wall of the catheter defines a passage 28, through which a guide wire 15 can be inserted by which the catheter can be guided, as shown in FIGS. 1 and 3. A multi-lobed balloon 30 is mounted on and around the shaft of the catheter at its distal end portion 27. FIG. 3 is a longitudinal section of the catheter 20 of FIG. 1 taken along the line 3—3. As shown in FIG. 3, there is a recessed area 27a at the proximal aspect of the distal end 27 into which a proximal end 30a of the balloon 30 is secured by bonding. A distal end 30b of the balloon 30 is secured by bonding at a recessed area 27b on the distal aspect of the distal end 27. The process of bonding is well known to the prior art. In the illustrative embodiment shown in FIGS. 1 and 2, the flow passage 22 terminates short of the far distal end of the catheter, and a radial passage 24 communicates between the passage 22 and the interior 32 of the balloon 30. Other means may be provided for establishing communication between the multi-lobed balloon and a flow passage, the process of inflating balloons of balloon dilation catheters being well known. The multi-lobed balloon 30 is inflated by injecting a liquid via the flow passage 22. In its preferred embodiment, the multi-lobed balloon is comprised of two portions. The first portion is a continuous balloon portion 29 of preferably compliant balloon material, for example polyolefin and the second portion is made up of a plurality of strips 31a through 31d, of relatively less compliant balloon material, for example polyethylene terephthalate, radially spaced and arranged longitudinally over the long axis of the continuous balloon portion, superposed upon the continuous balloon. FIG. 2 illustrates four strips 31a, 31b, 31c and 31d overlying the continuous balloon portion 29. The four strips, 31a through 31d divide the continuous balloon 29 into eight sections; sections 29a, 29b, 29c and 29d, which underlie the strips 31a, 31b, 31c and 31d respectively and sections 29e, 29f, 29g and 29h, which do not underlie the strips. Each of the strips 31a through 31d is secured to the catheter shaft proximal and distal to proximal and distal ends of the continuous balloon 29, by means of thermal bonding or adhesive bonding or by other means well known to the prior art. FIG. 3 illustrates the strips 31a and 31c. The proximal end of the strip 31a is secured to the distal end 27 of the catheter 25 at 21a. The distal end of the strip 31a is secured to the catheter at 41a. Similarly the proximal and distal ends of the other strip 31c are secured to the catheter at 21c and 41c respectively. Although not shown in the FIG. 3, the proximal and distal ends of strips 31b and 31d are similarly bonded to the catheter shaft, proximal and distal to the continuous balloon portion 29. Each of the strips 31a through 31d may also be bonded to the continuous balloon portion 29. When the continuous balloon portion 29 is inflated, the sections 29a, 29b, 29c and 29d, underlying the strips 31a, 31b, 31c and 31d respectively do not expand as much as the sections 29e, 29f, 29g and 29h, thereby providing a multi-lobed shape to the balloon. In another embodiment, instead of strips 31a through 31d, wires or strings of plastic or other material may be used to restrict complete expansion of continuous balloon portion 29, so as to provide the balloon with the multi-lobed shape. As can be appreciated by those skilled in this art, by varying the type of compliant and non compliant materials used, the balloon 30 may appear cylindrical at low pressures and assume a multi-lobed shape at higher pressures. Alternatively still, by making continuous balloon 29 of a non compliant material, having alternating longitudinally extending regions of thin and thicker material, for example, having thinner sections 29a, 29b, 29c and 29d, and having the strips 31a, 31b, 31c and 31d of compliant material, the balloon may appear multi-lobed at low inflation pressure and cylindrical at higher inflation pressures. This embodiment is particularly desirable in soft lesions, whereby a smooth cylindrical shape of the balloon provides smooth inner surface to the dilated stenosis. In yet another embodiment, the balloon material may be composed of alternating regions of compliant and non compliant balloon materials, corresponding to the thin and the thick portions respectively, these portions bonded together at their shoulders. As illustrated in FIG. 2A, when the balloon 30 is expanded initially inside a stenotic region 55 of the coronary artery 50, the balloon 30 expands to a preselected configuration or to the configuration of the stenosis, depending upon the size of the lumen inside the stenosis. On further inflation as illustrated in FIG. 2b, only the lobed portions 29e, 29f, 29g and 29h, expand further. The areas of stenosis, being compressed by these lobes of the balloon are under higher radial pressure as compared with the areas of stenosis being compressed by the intervening sections 29a, 29b, 29c and 29d. The alternating areas of high and low radial pressure inside a stenotic region increase the number of cracks, as illustrated at 60 in FIG. 2B, in the stenotic regions compared to a conventional balloon. For a desired post angioplasty lumen, increased numbers of superficial cracks created by the balloon of the present invention translate into fewer deeper cracks created by the conventional balloons. Advantageously, the superficial cracks prevent dissection and rupture of the artery. More advantageously, the superficial cracks limit the extent of medial injury and hence reduce the incidence of restenosis. The multi-lobed balloon of the present invention is more likely to create cracks in the hard region of stenosis than the conventional balloon. The lobes 29e, 29f, 29g and 29h of the balloon of the present invention act as anchors inside the hard region of the stenosis, preventing slippage of the balloon into the soft regions of the stenosis and cause cracks in the hard region as well. Advantageously, the coronary artery stenosis dilated by the multi-lobed balloon of the present invention is less likely to recoil because the cracks are as likely located in the hard region of the stenosis as they are in the soft region of the stenosis. Furthermore, since the radial pressure is interrupted along the inner circumference of the stenosis of the artery, thereby, the cracks are more likely created in the areas of the stenosis between the adjacent lobes, for example crack 60 in the stenosis 55 occurring between the lobes 29g and 29h. Advantageously, such crack extends along the long axis of the blood vessel in a lengthwise direction rather than spiral or transverse or zigzag fashion. The arterial tissue neighboring the longitudinally extending cracks is less likely to obliterate blood flow through the arterial lumen than the tissue neighboring cracks which are not longitudinal, thereby minimizing the risk of acute closure associated with prior art angioplasty catheters further.

What is claimed is:

1. A balloon dilation catheter for treatment of stenosis inside a hollow body lumen, comprising a catheter tube, an inflatable balloon mounted on and at least partially around said catheter tube, said balloon having a multiplicity of lobes extending longitudinally of said tube and, when inflated, spaced radially from said tube through at least a portion of their length, said lobes being defined by intermediate strips of material less compliant than the areas of the balloon between said intermediate strips, and said lobes between said intermediate strips becoming larger relative to said intermediate strips when said balloon is further inflated.

2. The balloon dilation catheter of claim 1 wherein the intermediate strips are superposed on a balloon of uniform wall thickness and material.

3. The balloon dilation catheter of claim 2 wherein the balloon and the intermediate strips are secured to the catheter tube at distal and proximal ends of the balloon.

4. The balloon dilation catheter of claim 2 wherein the intermediate strips are secured to the balloon only at the distal and proximal ends thereof.

* * * * *